United States Patent [19]

Gonzales

[11] Patent Number: 5,131,537
[45] Date of Patent: Jul. 21, 1992

[54] FLEXIBLE TIP TRAY PACKAGING FOR MEDICAL CATHETERS

[75] Inventor: Rolando J. Gonzalez, Cooper City, Fla.

[73] Assignee: Cordis Corporation, Miami Lakes, Fla.

[21] Appl. No.: 771,149

[22] Filed: Oct. 3, 1991

[51] Int. Cl.⁵ ............................................. B65D 85/08
[52] U.S. Cl. .................... 206/364; 206/439; 206/564
[58] Field of Search ............... 206/364, 439, 563, 564

[56] References Cited

U.S. PATENT DOCUMENTS

| | | | |
|---|---|---|---|
| 2,947,415 | 8/1960 | Garth | 206/364 |
| 3,851,649 | 12/1974 | Villari | 206/564 |
| 3,967,728 | 7/1976 | Gordon et al. | 206/364 |
| 4,779,727 | 10/1988 | Taterka et al. | 206/364 |
| 4,923,061 | 5/1990 | Trombley, III | 206/364 |

Primary Examiner—William I. Price
Attorney, Agent, or Firm—Lockwood, Alex, Fitzgibbon & Cummings

[57] ABSTRACT

Packaging for medical catheters is provided which includes a flexible tip tray that is made of a material having a hardness value significantly less than that of medical catheters to be packaged within the sterilizable packaging. The flexible tip tray includes a flexible groove having a cross-sectional size which accomodates medical catheters of different French sizes. The flexible tip tray does not damage the catheter of any such size when the catheter is removed from the packaging by sliding same out of the flexible tip tray, which remains within the packaging during this procedure in order to avoid handling of the flexible tip tray by a member of the surgical team using the medical catheter.

12 Claims, 1 Drawing Sheet

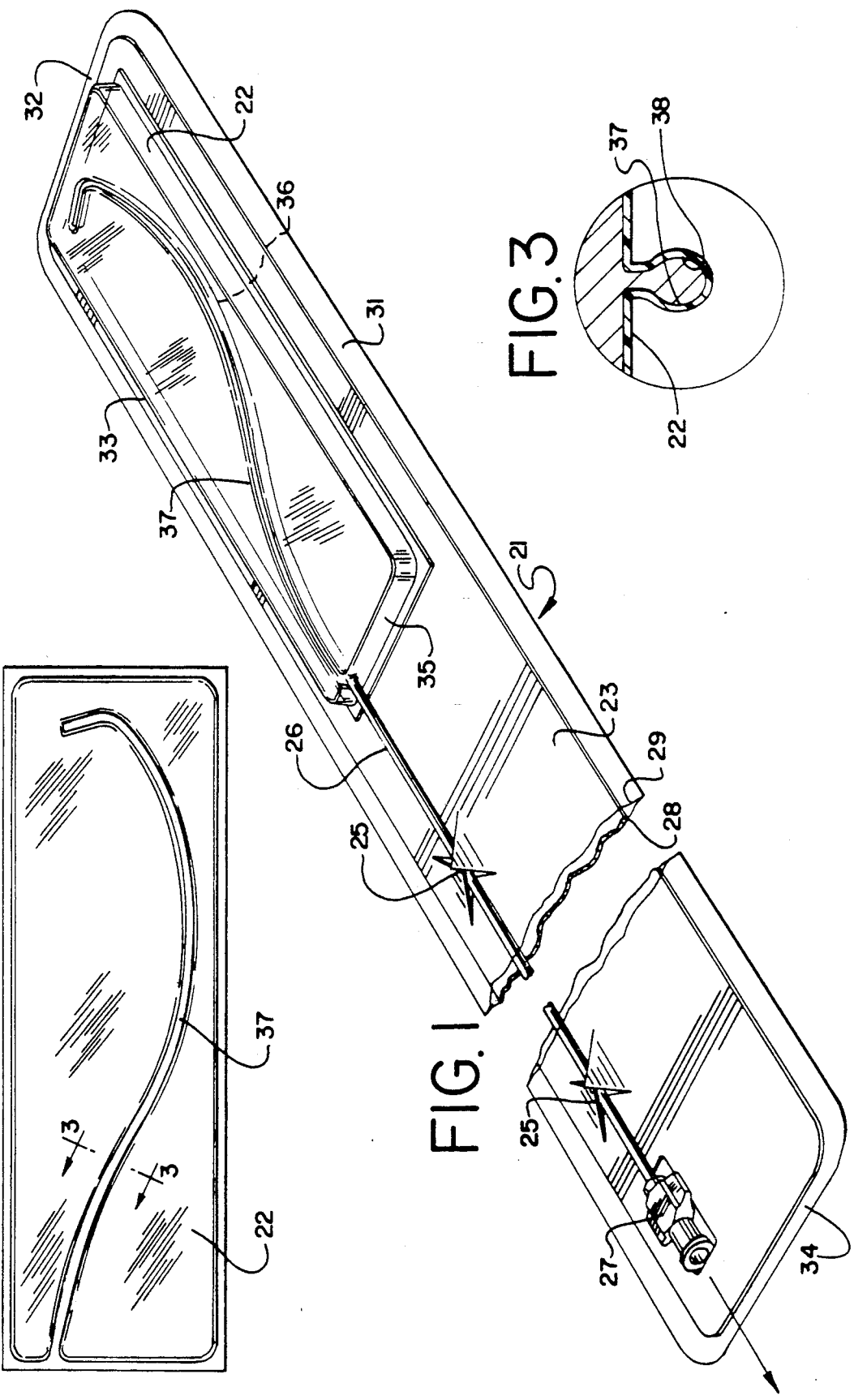
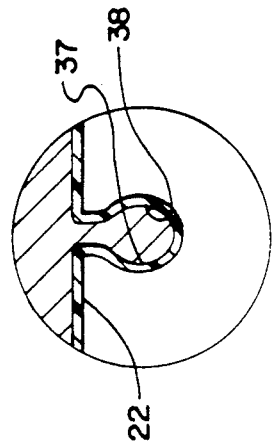

FLEXIBLE TIP TRAY PACKAGING FOR MEDICAL CATHETERS

BACKGROUND AND DESCRIPTION OF THE INVENTION

The present invention generally relates to packaging for medical devices, especially to packaging which includes a flexible tip tray for temporarily supporting a curved tip portion of a medical catheter. More particularly, the invention relates to sterilizable packaging for medical catheters, which packaging includes a flexible tip tray made of a material having a hardness value which is less than that of the elongated medical catheter packaged thereby The flexible tip tray includes a flexible groove having a curved plan configuration corresponding to the shape of the curved tip portion of the medical catheter and having a cross-section including a circular portion for encircling the medical catheter. The flexible tip tray rests upon an elongated mounting card positioned within an enclosed elongated pouch. The walls of the flexible groove of the flexible tip tray readily expand and contract so as to accommodate catheters of differing French sizes while allowing for sliding removal of the catheter tip portion therefrom without damaging or deforming the curved catheter tip portion Certain catheters include tip portions having curved configurations which are designed for facilitating passage of the catheter into and through body passageways such as the lumen of a blood vessel, a heart passageway, and the like, often with fluoroscopic guidance. Surgeons and medical teams have come to rely upon catheter tip portions having specially designed shapes, and it is important that these shapes be maintained to close tolerances after manufacturing and sterilization has been completed. This includes maintaining the shape during transport and storage such as by providing a tip tray which is intended to protect and maintain the curve of the tip portion of the medical catheter. It is also important that the curved tip configuration be maintained without damage to the catheter not only during transport and storage but also when the curved tip portion is removed from the tip tray just prior to implementation of a medical procedure such as angioplasty.

Medical catheters must exhibit adequate flexibility so that the tubing thereof can easily wind its way through body passageways which include bends and the like whereby the catheter can traverse a pathway through, for example, branching blood vessels and curved pathways within and into blood vessels, body cavities, organs and the like. Furthermore, in many instances, a catheter is manipulated from a proximal location outside of the body in order to position the distal portion of it in the vicinity of the administration or treatment location. In such systems or assemblies, it is important that the catheter exhibit adequate torque control so that it can be manipulated through narrow and branching passageways by radial movements and the like while having enough longitudinal or column resistance to negotiate through these passageways. This being the case, it is important that the catheter be made of a material meeting certain flexibility and stiffness characteristics at the same time. Particularly suitable in this regard are certain polyurethane materials that are especially advantageous for many uses, particularly with respect to catheters for angioplasty treatments. An ideal tip tray packaging component should be able to perform the necessary shaping and protecting function without damaging materials such as the polyurethanes that are well-suited for angioplasty catheters and the like. Accordingly, it is important that tip trays do not cause any damage to the curved tip portion of the catheter, either during insertion into, storage within, or removal from the tip tray.

Besides concerns regarding prevention of damage to the curved catheter tip portion, tip trays can interfere with easy and rapid removal of the catheter from the packaging therefor. Often, the tip tray slides out of the pouch-like packaging together with the catheter. This requires a member of the medical team to separately handle and dispose of the tip tray itself, as well as the rest of the packaging for the catheter. Accordingly, it would be advantageous to provide a catheter packaging assembly which includes a tip tray that remains within the packaging pouch even upon removal of the curved tip catheter from the pouch and from the tip tray within the pouch.

The present invention provides packaging for medical catheters which incorporates a flexible tip tray that forms the curved tip portion of a catheter while being able to accommodate catheters of different French sizes. The flexible tip tray also has a hardness value less than and a flexibility greater than that of the curved catheter tip portion, which is contrary to prior art tip trays made of generally rigid and substantially inflexible material. The flexible tip tray is a component of a packaging assembly including an elongated pouch and an elongated mounting card positioned within the enclosed elongated pouch. The flexible tip tray rests upon the elongated mounting card within the elongated enclosed pouch. When the curved tip catheter is removed from the pouch, the curved tip slidingly passes through the curved groove of the flexible tip tray. Due in large measure to the flexibility of the flexible tip tray, the tray maintains interference engagement with other components of the packaging and is retained within the pouch even while the curved tip portion of the catheter slides along and through the curved groove of the flexible tip tray when the medical team member pulls the catheter out of the pouch.

It is accordingly a general object of the present invention to provide improved packaging for medical catheters that includes a flexible tip tray component.

Another object of the present invention is to provide an improved flexible tip tray that accommodates catheters of differing French sizes without in any way damaging the catheters.

Another object of this invention is to provide an improved catheter packaging assembly that minimizes the chance of developing ovality characteristics within the curved catheter tip portion.

Another object of the invention is to provide an improved tip tray packaging component molded within a master mold having a groove with a precise elongated curve and configuration and a cross-section shape which accommodates multiple French sizes.

These and other objects, features and advantages of the invention will be clearly understood through a consideration of the following detailed description.

BRIEF DESCRIPTION OF THE DRAWINGS

FIG. 1 is a perspective view of the preferred packaging assembly, partially broken away, in accordance with the invention;

FIG. 2 is a top plan view of the flexible tip tray component of the packaging illustrated in FIG. 1; and FIG. 3 is a cross-sectional view along the line 3—3 of FIG. 2.

DESCRIPTION OF THE PARTICULAR EMBODIMENTS

The preferred packaging assembly illustrated in FIG. 1 is generally designated by reference numeral 21. It includes a flexible tip tray 22 which will be described in greater detail hereinafter. Also included are an elongated mounting card 23 and an elongated pouch or overwrap 24, both of which are of generally known construction.

The elongated mounting card 23 includes at least one cross-foot serration 25 relatively closely spaced from an edge of the flexible tip tray 22 resting on the elongated mounting card 23. Typically, a plurality of cross-foot serrations 25 will be provided and spaced generally along the length of the elongated mounting card, the number of cross-foot serrations 25 being selected so as to adequately support a catheter 26. More particularly, the catheter 26 passes through at least a portion of each cross-foot serration as illustrated in FIG. 1 so that the catheter 26 is generally threaded through the elongated mounting card 23 and secured thereto in a manner which permits easy removal of the catheter 26 from off of the elongated mounting card 23 when desired. It will be noted that the removal can be by way of sliding the length of the catheter 26 generally along the elongated mounting card and generally through each cross-foot serration 25. Inasmuch as a typical catheter 26 includes a hub 27, the sliding movement of the catheter 26 out of the packaging assembly 21 will be in the direction of the arrow included in FIG. 1.

Regarding the elongated pouch or overwrap 24, this may be of any suitable construction which facilitates sterilization, packaging and storage. A typical construction in this regard includes two generally flexible sheet members 28, 29 along the edges 31, 32, 33, 34 of the elongated pouch or overwrap 24. In a typical arrangement in this regard, one sheet member 28 is made of cellulosic material and is generally opaque, while the other sheet member 29 is made of a polymeric material and is generally transparent. Details of the materials suitable in this regard are known in the art. The same is true for the elongated mounting card 23, a preferred material in this regard being a cellulosic material such as a cardboard or fiberboard, preferably including a thin polymeric coating on a least one side thereof, typically the side onto which the catheter 26 is mounted.

Regarding the flexible tip tray 22, it is fully enclosed within the elongated pouch or overwrap 24 and it rests upon the top surface of the elongated mounting card 23. Due primarily to the flexible attributes of the flexible tip tray 22, the flexible tip tray 22 will remain within the package assembly 21 when the catheter 26 is removed from the packaging assembly 21 by the relative sliding movement illustrated by the arrow in FIG. 1. It has been found that the leading edge 35 of the flexible tip tray 22 will, upon implementation of this relative movement, engage cross-foot serration 25. This engagement, coupled with the fact that the flexible tip tray and elongated mounting card are confined within the elongated pouch or overwrap, permit a member of the medical team to slidingly remove the catheter 26 from the pouch while the flexible tip tray 22 remains within the elongated pouch or overwrap 24. Furthermore, this removal is accomplished in a manner that does not damage the tip portion 36 of the catheter 26. Heretofore known rigid tip trays, typically made of high impact styrene or of polyvinylchloride or the like, do not possess these desirable attributes.

Another desirable attribute which is not possessed by previously known and used tip trays but which is possessed by the packaging assembly 21 including the flexible tip tray 22, is the ability of the flexible tip tray 22 to accommodate catheters of different sizes. For example, the flexible tip tray 22 can accommodate catheters of French sizes 6, 7 and 8. Typically, this is accomplished by molding the flexible tip tray 22 out of a flexible material such that it has a curved groove 37 having a generally circular cross-section 38 having an inner diameter that is substantially identical to the outer diameter of a French 6 size catheter. The curved groove 37 also has a curved configuration, in plan view, that corresponds to the shape desired of the curved tip portion 36 of the catheter 26. Typically, during manufacturing, the tip end portion of a catheter will undergo a final shaping procedure during sterilization. More specifically, the curved groove 37 has a shape which is made from a master mold having the configuration desired and needed for the particular catheter being manufactured. The tip end portion of the catheter being manufactured is placed within the groove while the rest of the catheter is placed within the packaging assembly 21. Thereafter, sterilization is carried out at an elevated temperature, as a result of which the catheter will, after cooling, take on the shape of the curved groove 37.

With more particular reference to the advantageous flexibility feature imparted by the flexible tip tray, the walls of the curved groove 37 readily move apart along the open portion of the curved groove in order to accommodate catheters having respective outside diameters larger than the inside diameter of the generally circular cross-section 38. In the illustrated example where the diameter of the generally circular cross-section 38 corresponds to a French 6 sized catheter, the curved groove 37 will flexibly open in order to accommodate catheters of a larger French size, including French 7 and French 8 sized catheters. Furthermore, this opening up of the curved groove 37, because of the flexible nature of the flexible tip tray 22, maintains a fit which is close but non-restricting generally around the circumference of even the larger sized catheters. This is an important feature inasmuch as it is extremely important that a catheter, such as one intended for angioplasty uses, is not forced to take on a cross-sectional shape other than a circular one. With a rigid tip tray, a catheter will develop ovality if the catheter has an outer diameter larger than that to which the rigid tip tray was molded. In other words, the catheter will develop an out-of-round condition. This ovality condition affects the pressure of injection during surgical procedures when radiopaque material is injected, thereby causing a situation where the even and consistent flow properties designed into the catheter could be disrupted.

Regarding the flexibility attribute of the flexible tip tray 22, the molded flexible tip tray must have a flexibility such that its tensile strength and hardness values are less than those of the catheter 26, and particularly of its curved portion 36, to be inserted within the packaging assembly 21. When the packaging assembly 21 is intended to house a polyurethane catheter, a preferred material for the flexible tip tray 22 is a material which provides good puncture resistance and a good vapor barrier, as well as a certain degree of adhesion in order to increase the co-efficient of friction between the flexible tip tray 22 and the elongated mounting card 23. For example, when the mounting card has a coating of polyethylene on its top surface, it is advantageous that the flexible tip tray 22 also have a polyethylene layer on the surface thereof which engages the top surface of the elongated mounting card. A preferred material for a flexible tip tray is a co-extrusion of polyethylene or other polyolefin co-extruded with a Surlyn film or other film which provides both puncture resistance and a good vapor barrier. Generally speaking, it is advantageous that the material of the flexible tip tray be significantly more flexible or less rigid than the medical catheter in order that flexing of the curved groove 37 will be easily accomplished without any risk of damage to the catheter. For example, for a typical medical device catheter such as one made of medical-grade polyurethanes, the material for a flexible tip tray having a thickness ranging between about 0.003 and about 0.016 inch should have a tensile strength within the range of between about 3350 and about 3660 pounds per square inch.

It will be understood that the embodiment of the present invention which has been described is merely illustrative of an application of the principles of the present invention. Numerous modifications may made by those skilled in the art without departing from the true spirit and scope of the invention.

I claim:

1. Sterilizable packaging for an elongated medical catheter, comprising:
   an elongated pouch including elongated generally flexible sheet members secured together along respective edges of the sheet members so as to form an enclosed elongated pouch;
   an elongated mounting card positioned within said enclosed elongated pouch, said elongated mounting card lying substantially flat within said enclosed elongated pouch and including at least one cross-foot serration means at a location along the length of said elongated mounting card, said cross-foot serration means being for receiving and securing an elongated medical catheter onto said elongated mounting card and within said enclosed elongated pouch; and
   a flexible tip tray positioned within the enclosed elongated pouch at a location whereby the flexible tip tray generally rests upon an end portion of the elongated mounting card, said flexible tip tray having a flexible groove for receiving and securing a curved tip portion of the elongated medical catheter at a location spaced from the cross-foot serration means, said flexible tip tray having a hardness value which is less than that of the elongated medical catheter, said flexible groove having a cross-sectional size which accommodates medical catheters of different French sizes, said flexible groove further having a plan configuration corresponding to the curved tip portion of the elongated medical catheter.

2. The sterilized packaging in accordance with claim 1, wherein said flexible tip tray has a tensile strength of between about 3350 and about 3660 pounds per square inch.

3. The sterilizable packaging in accordance with claim 1, wherein said flexible tip tray has a thickness of between about 0.003 and about 0.016 inch and a tensile strength of between about 3350 and about 3660 pounds per square inch.

4. The sterilizable packaging in accordance with claim 1, wherein said flexible groove of the flexible tip tray has flexible walls which generally move apart from one another in response to engagement by the medical catheter positioned therewithin.

5. The sterilizable packaging in accordance with claim 1, wherein the flexible tip tray and flexible groove are made of a film coextrusion of a polyolefin and a flexible film having puncture resistance and vapor barrier properties.

6. The sterilizable packaging in accordance with claim 3, wherein the flexible tip tray and flexible groove are made of a film coextrusion of a polyolefin and a flexible film having puncture resistance and vapor barrier properties.

7. A flexible tip tray component of sterilizable packaging for an elongated medical catheter, the sterilizable packaging including an enclosed elongated flexible pouch and an elongated mounting card positioned within the enclosed elongated pouch, the flexible tip tray being positioned within the enclosed elongated pouch at a location whereby the flexible tip tray generally rests upon an end portion of the elongated mounting card, said flexible tip tray comprising a molded member having a top surface and a bottom portion, the top surface including a flexible groove for receiving and securing a curved tip portion of the elongated medical catheter, said flexible tip tray having a hardness value which is less than that of the elongated medical catheter, said flexible groove having a cross-sectional size which accommodates medical catheters of different French sizes, said flexible groove having a plan configuration corresponding to the curved tip portion of the elongated medical catheter.

8. The flexible tip tray in accordance with claim 7, wherein said flexible tip tray has a tensile strength of between about 3350 and about 3660 pounds per square inch.

9. The flexible tip tray in accordance with claim 7, wherein said flexible tip tray has a thickness of between about 0.003 and about 0.016 inch and a tensile strength of between about 3350 and about 3660 pounds per square inch.

10. The flexible tip tray in accordance with claim 7, wherein said flexible groove of the flexible tip tray has flexible walls which generally move apart from one another in response to engagement by the medical catheter positioned therewithin.

11. The flexible tip tray in accordance with claim 7, wherein the flexible tip tray and flexible groove are made of a film coextrusion of a polyolefin and a flexible film having puncture resistance and vapor barrier properties.

12. The flexible tip tray in accordance with claim 9, wherein the flexible tip tray and flexible groove are made of a film coextrusion of a polyolefin and a flexible film having puncture resistance and vapor barrier properties.

* * * * *